United States Patent [19]

Salem

[11] 4,092,982
[45] June 6, 1978

[54] THERAPEUTIC WRAP

[76] Inventor: Nazih M. N. Salem, 1312 Raintree Cir., Culver City, Calif. 90230

[21] Appl. No.: 677,832

[22] Filed: Apr. 16, 1976

[51] Int. Cl.$^2$ ............................................. A61N 15/00
[52] U.S. Cl. ..................................... 128/82.1; 128/402
[58] Field of Search .................. 128/82.1, 399, 402, 128/403, 165

[56] References Cited

U.S. PATENT DOCUMENTS

| | | | |
|---|---|---|---|
| 3,149,943 | 9/1964 | Amador | 128/402 X |
| 3,175,558 | 3/1965 | Caillouette et al. | 128/403 |
| 3,429,315 | 2/1969 | McDonald | 128/402 |
| 3,506,013 | 4/1970 | Zdenek | 128/402 |
| 3,717,145 | 2/1973 | Berndt et al. | 128/82.1 |
| 3,900,035 | 8/1975 | Welch et al. | 128/402 |

Primary Examiner—John D. Yasko

[57] ABSTRACT

A therapeutic wrap comprising an outer strip being of an elongated, resilient elastic bandage and an inner strip of flexible material formed into a pocket or pockets having a partially secured overlapping flap, said pocket or pockets containing prepackaged cooling materials. The inner and outer strips are attached at one end and nominally secured to each other along their length by at least one loop attached to the strip of pockets and encircling the resilient bandage, whereby the loops do not inhibit the resilient movement of the outer strip.

4 Claims, 8 Drawing Figures

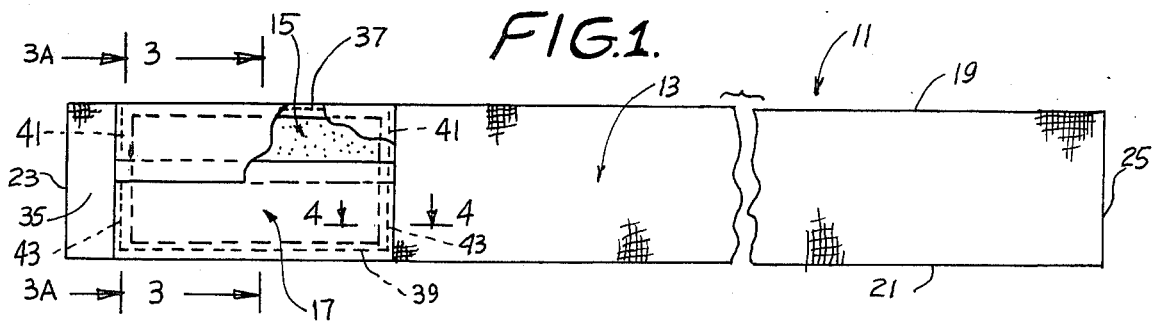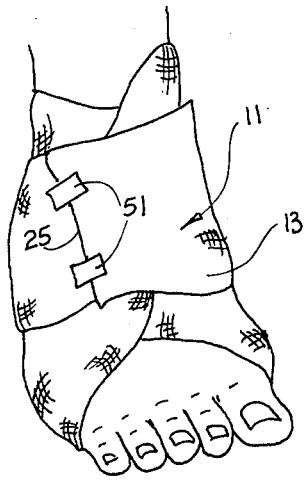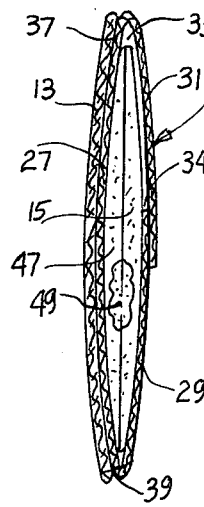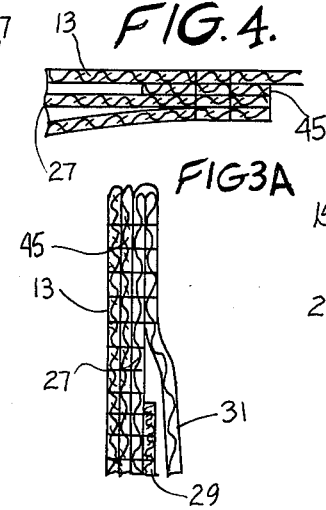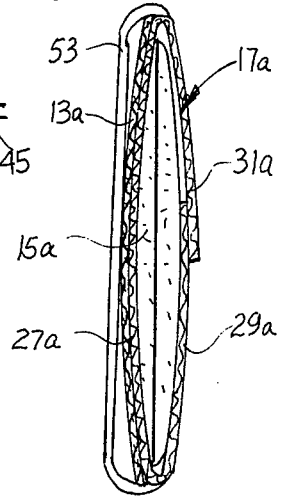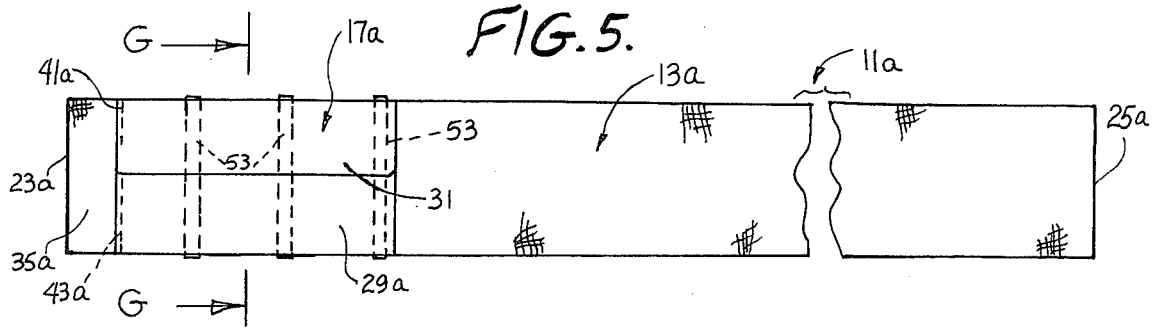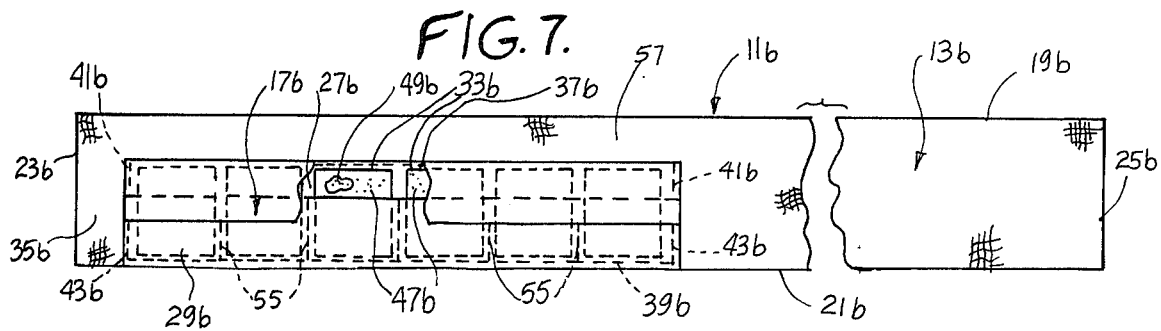

THERAPEUTIC WRAP

BACKGROUND OF THE INVENTION

This invention comes within the field of therapeutic wrap devices for compression and heat removal by chilling for treating various bodily afflictions, injuries, diseases, ruptures, traumas, and lacerations.

The present invention more specifically comes within the field of devices that combine these two elements into a single wrap and thereby into a single application operation.

The present invention is distinguished from the prior art by the manner of construction obtaining between the cooling material pocket or pockets and the wrap. The prior art is deficient in providing maximum combination of the separate features of compression and cooling. Usually compression features are sacrificed for cooling features by virtue of the awkwardness of pocket or pockets to wrap construction. The present invention by virtue of the pocket or pockets to wrap construction allows for the maximum utilization, without deficiencies relative to conventional standards, of compression, cooling and vigorous handling.

In addition, this arrangement when utilizing the special pocket to wrap construction and the partially secured overlapping flap, provides a more comfortable limitlessly flexible, nonrestrictive, support than the nonelastic devices typical of this prior art.

SUMMARY OF THE INVENTION

The present invention allows for the maximum utilization of both compression and cooling by providing a resilient elastic strip uninterrupted by stitching or other immpedimenta to which, at one end, is attached another strip running coincidental to the resilient strip. This second strip is a pocket or is a series of pockets along which loops are attached and through which loops said resilient strip runs and is therefore nominally secured along its length to the second strip.

By this arrangement, the maximum compression is realized from the uninterrupted resilience of the elastic strip and by the nominal pressure of said loops pulling the said pockets, which contain coolant, into and around an afflicted body area. In addition, an elastic strip could be provided which is substantially longer than the second strip of pockets, so that this greater length could be brought on around and wrapped over the second strip thereby providing an even greater compression and security of attachment to the afflicted body area.

Also, the present invention provides a special flap on the pocket or pockets consisting of a partially secured overlapping flap. This flap allows for easy insertion and removal of the various sized prepackaged coolants of manufacture. At the same time, the special flap prevents accidental falling out of the coolant packages, even with vigorous handling.

None of the disadvantages, of the interrupted single strip pockets, which distinguishes the prior art, occur in the present invention. The pesent invention is distinguished by its ease of adaptability in accepting the various sized prepackaged coolants.

It is distinguished over the prior art by its ability to withstand vigorous handling, not only in an unrushed therapeutic setting, but in an emergency setting as well.

The prior art is limited in flexibilities when dealing with the larger prepackaged coolants in that in order for these packages to be held securely in a pocket, the pocket must be sewn on all four sides, in which case great awkwardness is encountered in washing a soiled wrap and in refreezing the coolant. If the pocket is secured on three sides only, then vigorous handling of the wrap is impossible.

By providing a wrap with a pocket or pockets having special partially secured overlapping flap for insertion and removal of the cooling material, the wrap can be used for either compression alone or compression and cooling. This feature is advantageous also for allowing for the separate cooling of the cooling package by any of the various means including insertion in a refrigerator or freezer type device or cooling by means of actuating together two or more materials.

The pocket can be constructed of various materials. However, a soft cloth, such as flannel is preferred. A soft cloth will not cause discomfort to the injured region and will provide some insulating effect to prevent making the injured region too cold.

If the pocket is located adjacent one end of the bandage, but spaced inwardly therefrom, a section of the bandage between the pocket and the end of the bandage is left uncovered. This provides a gripping section which can be manually grasped to facilitate positioning and installation of the therapeutic wrap.

The pocket is preferably no wider than about the width of the bandage. Although the pocket could be wider than the bandage, its edges would then protrude beyond the bandage and this would provide a less attractive therapeutic wrap. In addition, to the extent that the pocket extends beyond the side edges of the bandage, no compressive force would be available at those regions.

The prior art is distinguished also by the susceptibility of weakening the security of its stitching by pressure encountered when the wrap is stretched. The present invention, when it takes the form double strip, does not encounter pressure along its stitching, because there is no stitching on the bandage itself, except at one end, which by virtue of its end positioning, receives only the slightest transverse pressure in the operation of application.

The present invention, in distinction to the prior art utilizes a narrow intermediate reinforcing material or tape between the pocket and bandage giving a ratio of stretchability to strain or stitching which is far superior to the prior art.

The invention, together with further features and advantages thereof, can best be understood by reference to the following description taken in connection with the accompanying illustrative drawing.

BRIEF DESCRIPTION OF THE DRAWING

FIG. 1 is a plan view of the therapeutic wrap constructed in accordance with the teachings of this invention with a portion of the pocket being broken away.

FIG. 2 is a perspective view showing the therapeutic wrap in use.

FIG. 3 is an enlarged sectional view taken generally along line 3—3 of FIG. 1.

FIG. 3A is an enlarged, fragmentary sectional view taken generally along line 3A—3A of FIG. 1.

FIG. 4 is an enlarged, fragmentary sectional view taken generally along line 4—4 of FIG. 1.

FIG. 5 is a plan view of a second embodiment of therapeutic wrap constructed in accordance with the teachings of this invention.

FIG. 6 is an enlarged sectional view taken generally along line 6—6 of FIG. 5.

FIG. 7 is a plan view of a third embodiment of therapeutic wrap constructed in accordance with the teachings of this invention and with a portion of the pocket broken away.

DESCRIPTION OF THE PREFERRED EMBODIMENTS

FIG. 1 shows a therapeutic wrap 11 which generally includes a bandage 13, a refrigerant gel package 15, and a pocket 17 for carrying the refrigerant gel package on the bandage 13. The bandage 13 is in the form of an elongated flexible strip which is resilient in the direction of its elongation. The bandage 13 may be an elastic cloth bandage of conventional construction. The bandage 13 in the embodiment illustrated is rectangular and has side edges 19 and 21 and end edges 23 and 25.

The pocket 17 can be of various different constructions, and in the embodiment illustrated it includes a back wall 27 (FIG. 3), a front wall 29 integrally joined to the back wall, and a front flap 31 integrally joined to the back wall and overlapping an upper edge portion of the front wall. The pocket 17 can be opened to provide access to the compartment 33 through an opening 34 in the front wall 29 by lifting the lower edge of the front flap 31.

In the embodiment illustrated, the pocket 17 is adjacent the end edge 23. The left edge (as viewed in FIG. 1) of the pocket 17 is spaced inwardly from the end edge 23 to provide a relatively narrow gripping section 35. The pocket 17 in the embodiment illustrated is of approximately the same width as the bandage 13 and the longitudinal edges of the pocket generally coincide with the side edges 19 and 21, respectively, of the bandage 13. By way of example, the gripping section 35 may be of the order of 1 to 2 inches in width, and the pocket 17 may be remotely located relative to the end edge 25.

The pocket 17 may be attached to the bandage 13 in various ways. In the form shows in FIGS. 1-4, the pocket is attached to the bandage 13 by stitching which extends along an upper seam 37, a lower seam 39, upper side seams 41 and lower side seams 43. The stitches along the upper seams 37 extend through the back wall 27 and the bandage 13 and along substantially the full length of the upper edge portion of the pocket 17. The stitching along the lower seam 39 extends through the front wall 29, and back wall 27, and the bandage 13 and along substantially the full length of the lower edge portion of the pocket 17.

Reinforcing material in the form of reinforcing tape 45 (FIGS. 3A and 4) lies between the back wall 27 and the bandage 13 along the side seams 41 and 43. The stitches along the upper side seams 41 extend through the flap 31, the back wall 27, the tape 45, and the bandage 13. The upper side seam 41 terminates above the upper edge of the front wall 29 to allow the flap 31 to be opened sufficiently to insert and remove the refrigerant gel or any cooling material package 15. The upper side seams 41 prevent the flap 31 from opening the pocket 17 inadvertently to allow the refrigerant gel or any cooling material package 15 to fall out of the pocket.

The stitching along the lower side seams 43 extends through the front wall 29, the back wall 27, the reinforcing tape 45, and the bandage 13. If desired, the reinforcing tape 45 can also be provided along the upper seam 37 and the lower seam 39.

The refrigerant gel or any cooling material package 15 includes container means in the form of a flexible, sealed, plastic bag or container 47 and refrigerant gel or any cooling material 49 within the container. The refrigerant gel or any other cooling material 49 in the embodiments of FIGS. 1-4 is preferably of the type which remains pliable at temperatures below freezing temperature of water. The container 47 is sealed so that none of the gel or any cooling material can escape.

In use, the refrigerant gel or any cooling material package 15 is removed from the pocket 17 and cooled to the desired temperature which may be below freezing point of water. The cooled refrigerant gel or any cooling material package 15 is reinserted into the compartment 33. The user then grips the therapeutic wrap 11 at the gripping section 35 and along another region of the bandage 13 and wraps the therapeutic wrap around the injured region being careful to place the refrigerant gel or any cooling material package 15 contiguous the injured region. As shown in FIG. 2, if the injured region is an ankle, the therapeutic wrap 11 may be applied to the ankle and foot as shown in FIG. 2. The end edge 25 of the bandage 13 is then attached to another portion of the bandage using conventional clips 51. Consequently, the injured ankle receives the necessary cooling action and compression.

FIGS. 5 and 6 show a therapeutic wrap 11a which is identical to the therapeutic wrap in all respects not shown or described herein. Portions of the therapeutic wrap 11a corresponding to portions of the therapeutic wrap 11 are designated by corresponding reference numerals followed by the letter a.

The primary difference between the therapeutic wrap 11 and 11a is the manner in which the pocket 17a is attached to the bandage 13. In the therapeutic wrap 11a, the stitching along the upper seam 37, the lower seam 39, and the side seams 41, and 43 along the righthand edge of the pocket 17a has been eliminated as a means for attaching the pocket to the bandage 13a; however, this stitching may be retained, if desired, for the purpose of sewing the pocket 17a together in the same manner as the pocket 17. In other words, if this stitching is retained, it does not extend into the bandage 13a. The edge of the pocket 17a adjacent the end edge 23a is attached to the bandage 13a by stitching along the upper side seam 41a and the lower side seam 43a. The pocket 17a may be sewn together in the same manner as the pocket 17 or it may be provided in any other way.

One or more retainers 53 (three being illustrated in FIG. 5) are attached to the pocket 17a in any suitable manner such as by sewing. Each of the retainers 53 extends along the back wall 27a and defines a loop therewith. The bandage 13a can be inserted through the loops, i.e. between the retainers 53 and the back wall 27a to thereby mount the pocket 17a on the bandage 13a. This allows the bandage 13a to move longitudinally relative to the pocket 17a. This form of mounting of the pocket 17a on the bandage 13a has the advantage of not inhibiting the resilience of the bandage.

FIG. 7 shows a therapeutic wrap 11b which is identical to the therapeutic wrap 11 in all respects not specifically shown or described herein. Portions of the therapeutic wrap 11b corresponding to portions of the therapeutic wrap 11 are designated by corresponding reference numerals followed by the letter b.

The primary difference between the therapeutic wrap 11b and the therapeutic wrap 11 is that the pocket 17b is divided into a plurality of compartments 33b and the container means for the refrigerant gel or any cooling material is divided into a corresponding number of containers 47b. In addition, the refrigerant gel or any cooling material 49b may be of the type which becomes solid and nonpliable at temperatures about 32° F.

As shown in FIG. 7, the pocket 17b is divided into a plurality of the compartments 33b by stitching extending along intermediate seams 55. The stitching along the intermediate seams 55 may correspond to the stitching along the lower side seams 43 in the embodiments of FIGS. 1-4 in that it extends through the front wall 29b, the back wall 27b, and the bandage 13b. Reinforcing tape (not shown) similar to the reinforcing tape 45 (FIG. 4) may be used along the seams 55, if desired. The stitching along the seams 37b, 39b, 41b, and 43b may be identical to the corresponding stitching described with reference to FIGS. 1-4.

Each of the containers 47b may be identical to the container 47 (FIGS. 1-4) except that the former is smaller and adapted to fit within one of the compartments 33b.

Another difference between the pockets 17 and 17b is that the latter is longer and narrower. The reduced width of the pocket 17b is merely illustrative and not essential. The reduced width of the pocket 17b provides an uncovered upper marginal region 57 of the bandage 13b and the lower edge of the pocket is substantially flush with the side edge 21b. The increased length of the pocket 17b permits additional containers 47b of refrigerant gel or any cooling material 49b to be inserted into the pocket. Although the pocket 17b is long and although the refrigerant gel or any cooling material 49b may be solid, the regions along the seams 55 intermediate adjacent compartments 33b form hinges which permit the therapeutic wrap 11b to be wrapped around an injured region.

The therapeutic wrap 11b can be used in the manner described above with reference to the therapeutic wrap 11 except that the therapeutic wrap 11b is particularly adapted for use on larger areas of the body. By selecting the compartments 33b in which a container 47b of refrigerant gel or any cooling material 49b is inserted, the cooling action can be obtained precisely at the desired location.

Although exemplary embodiments of this invention have been shown and described, many changes, modifications and substitutions may be made by one with ordinary skill in the art without necessarily departing from the spirit and scope of this invention.

I claim:

1. A therapeutic wrap consisting of an inner strip and an outer strip attached to each other along one end, the outer strip being an elongated resilient elastic compression bandage material, the inner strip being of flexible material formed into at least one pocket for receiving prepackaged coolants of manufacture, and running nominally coincidental with the outer strip, wherein at least one loop of flexible material is attached to the backside of the inner strip at intervals along its length; said at least one loop freely encircling the outer strip.

2. A therapeutic wrap consisting of an inner strip and an outer strip attached to each other along one end, the outer strip being an elongated resilient elastic compression bandage material, the inner strip being of flexible material formed into at least one pocket for receiving prepackaged coolants of manufacture, and running nominally coincidental with the outer strip, wherein the strip material is extended at the top forming a flap, the edge of which extends below the upper edge of the pocket lip, said flap having side edges, at least portions of said side edges of said flap being sewed to the pocket proper.

3. A therapeutic wrap consisting of an inner strip and an outer strip attached to each other along one end, the outer strip being an elongated resilient elastic compression bandage material, the inner strip being of flexible material formed into at least one pocket for receiving prepackaged coolants of manufacture, and running nominally coincidental with the outer strip, between which are situated at least one reinforcing tape strip, placed perpendicular to the length of the strips along which at least one seam runs, securing the two strips together.

4. A therapeutic wrap consisting of an outer elastic strip and inner strip of flexible material forming a pocket for receiving prepackaged coolants of manufacture, and running nominally coincidental with the length of the outer strip, said pocket includes a back wall confronting the elastic strip, a front wall having an opening therein, and a flap for covering said opening, said flap having side edges at least portions of said side edges of the flap being sewed to said back wall and joining the two strips together.

* * * * *